(12) United States Patent
Crapo et al.

(10) Patent No.: US 10,124,011 B2
(45) Date of Patent: Nov. 13, 2018

(54) METHODS OF TREATING ERECTILE DYSFUNCTION

(71) Applicants: BioMimetix JV, LLC, Englewood, CO (US); National Jewish Health, Denver, CO (US)

(72) Inventors: James D. Crapo, Englewood, CO (US); Rebecca Oberley Deegan, Omaha, NE (US)

(73) Assignees: BioMimetix JV, LLC, Englewood, CO (US); National Jewish Health, Denver, CO (US)

( * ) Notice: Subject to any disclaimer, the term of this patent is extended or adjusted under 35 U.S.C. 154(b) by 0 days.

(21) Appl. No.: 15/982,713

(22) Filed: May 17, 2018

(65) Prior Publication Data

US 2018/0264005 A1 Sep. 20, 2018

Related U.S. Application Data

(62) Division of application No. 14/892,740, filed as application No. PCT/US2014/053442 on Aug. 29, 2014, now Pat. No. 9,999,627.

(60) Provisional application No. 61/872,991, filed on Sep. 3, 2013.

(51) Int. Cl.

| | |
|---|---|
| *A61K 31/555* | (2006.01) |
| *A01N 59/20* | (2006.01) |
| *A01N 43/713* | (2006.01) |
| *A01N 59/16* | (2006.01) |
| *C09K 8/035* | (2006.01) |
| *A61K 8/19* | (2006.01) |
| *A61K 8/49* | (2006.01) |
| *A01N 55/02* | (2006.01) |
| *C09K 8/524* | (2006.01) |
| *C02F 5/12* | (2006.01) |
| *C11D 3/00* | (2006.01) |
| *A61Q 11/00* | (2006.01) |
| *A61K 45/06* | (2006.01) |
| *A61K 8/58* | (2006.01) |
| *C02F 103/42* | (2006.01) |
| *C02F 1/30* | (2006.01) |
| *C02F 1/32* | (2006.01) |
| *C02F 1/50* | (2006.01) |
| *C02F 103/02* | (2006.01) |

(52) U.S. Cl.
CPC ............ *A61K 31/555* (2013.01); *A01N 55/02* (2013.01); *A01N 59/16* (2013.01); *A01N 59/20* (2013.01); *A61K 8/19* (2013.01); *A61K 8/494* (2013.01); *A61K 8/58* (2013.01); *A61K 45/06* (2013.01); *A61Q 11/00* (2013.01); *C02F 5/12* (2013.01); *C09K 8/035* (2013.01); *C09K 8/524* (2013.01); *C11D 3/0078* (2013.01); *A61K 2800/58* (2013.01); *C02F 1/30* (2013.01); *C02F 1/32* (2013.01); *C02F 1/50* (2013.01); *C02F 2103/026* (2013.01); *C02F 2103/42* (2013.01); *C02F 2303/04* (2013.01); *C02F 2303/20* (2013.01); *C02F 2305/04* (2013.01); *C02F 2307/14* (2013.01)

(58) Field of Classification Search
CPC ...... A61K 31/555; A61K 31/23; A01N 59/20; A01N 43/713; A01N 59/16
See application file for complete search history.

(56) References Cited

U.S. PATENT DOCUMENTS

| | | |
|---|---|---|
| 3,936,385 A | 2/1976 | Cheng |
| 4,257,433 A | 3/1981 | Kwan |
| 4,865,545 A | 9/1989 | La Rocca |
| 5,061,106 A | 10/1991 | Kent |
| 5,152,686 A | 10/1992 | Duggan et al. |
| 5,785,523 A | 7/1998 | Overmyer |
| 5,939,051 A | 8/1999 | Santalucia et al. |
| 5,968,480 A | 10/1999 | Bergeron et al. |
| 5,989,526 A | 11/1999 | Aaslyng et al. |

(Continued)

FOREIGN PATENT DOCUMENTS

WO WO 00/43395 7/2000

OTHER PUBLICATIONS

International Search Report and Written Opinion, PCT/US2014/053442, dated Jan. 29, 2015.

(Continued)

*Primary Examiner* — Sahar Javanmard
(74) *Attorney, Agent, or Firm* — Myers Bigel, P.A.

(57) ABSTRACT

An active agent for use in a method of, or for use in the preparation of a medicament for, treating or inhibiting the development of erectile dysfunction and/or incontinence following pelvic radiation treatment in a subject in need thereof, comprising administering said subject an active agent in a treatment effective amount, is described. The active agent has the general structure of Formula I:

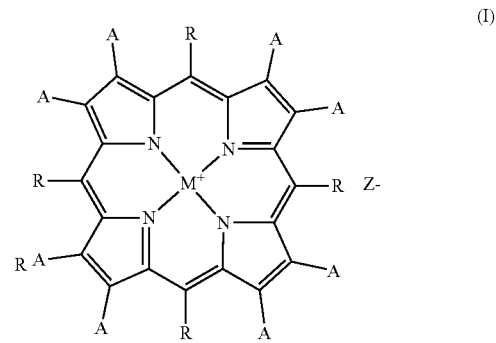

(I)

or a pharmaceutically acceptable salt thereof.

7 Claims, 3 Drawing Sheets

(56) References Cited

U.S. PATENT DOCUMENTS

| | | |
|---|---|---|
| 6,270,890 B1 | 8/2001 | Curtis et al. |
| 6,289,904 B1 | 9/2001 | Suhonen et al. |
| 6,416,744 B1 | 7/2002 | Robinson et al. |
| 6,479,477 B1 | 11/2002 | Crapo et al. |
| 6,514,483 B2 | 2/2003 | Xu et al. |
| 6,583,132 B1 | 6/2003 | Crapo et al. |
| 6,592,849 B2 | 7/2003 | Robinson et al. |
| 6,680,299 B2 | 1/2004 | Or et al. |
| 6,680,322 B2 | 1/2004 | Castelhano et al. |
| 6,680,324 B2 | 1/2004 | Castelhano et al. |
| 6,916,799 B2 | 7/2005 | Fridovich et al. |
| 7,025,950 B2 | 4/2006 | Majeti et al. |
| 7,229,286 B2 | 6/2007 | Jones et al. |
| 7,264,005 B2 | 9/2007 | Wong |
| 7,297,327 B2 | 11/2007 | Pilch et al. |
| 7,807,825 B2 | 10/2010 | Batinic-Haberle et al. |
| 8,183,364 B2 | 5/2012 | Batinic-Haberle et al. |
| 8,211,656 B2 | 7/2012 | Hyde et al. |
| 8,470,808 B2 | 6/2013 | Piganelli et al. |
| 8,513,305 B2 | 8/2013 | Davies |
| 2003/0229065 A1 | 12/2003 | Levy et al. |
| 2011/0262511 A1 | 10/2011 | Love et al. |
| 2012/0065181 A1 | 3/2012 | Warner et al. |
| 2016/0324868 A1 | 11/2016 | Ji et al. |

OTHER PUBLICATIONS

Oberley-Deegan RE et al. The antioxidant, MnTE-2-PyP, prevents side-effects incurred by prostate cancer irradiation. PLOS One. Sep. 2012; 7(9): e44178.

Batinic-Haberle et al. "Diverse functions of cationic Mn(III) N-substituted pyridylporphyrins, recognized as SOD mimics" *Free Radical Biology & Medicine* 51(5):1035-1053 (2011).

Black et al. "Current Concepts Regarding the Effect of Wound Microbial Ecology and Biofilms on Wound Healing" *The Surgical Clinics of North America* 90:1147-1160 (2010).

Burmølle et al. "Biofilms in chronic infections—a matter of opportunity—monospecies biofilms in multispecies infections" *FEMS Immunology & Medical Microbiology* 59:324-336 (2010).

Coenye et al. "In vitro and in vivo model systems to study microbial biofilm formation" *Journal of Microbiological Methods* 83:89-105 (2010).

Dall'Era et al. "Vascular endothelial growth factor (VEGF) gene therapy using a nonviral gene delivery system improves erectile function in a diabetic rat model" *International Journal of Impotence Research* 20:307-314 (2000).

Di Paola et al. "Reduced development of experimental periodontitis by treatment with M40403, a superoxide dismutase mimetic" *European Journal of Pharmacology* 516:151-157 (2005).

Flemming et al. "The biofilm matrix" *Nature Reviews Microbiology* 8:623-633 (2010).

Gauter-Fleckenstein et al. "Early and late administration of MnTE-2-PyP$^{5+}$ in mitigation and treatment of radiation-induced lung damage" *Free Radical Biology and Medicine* 48(8):1034-1043 (2010).

Karunakaran et al. "'Biofilmology': a multidisciplinary review of the study of microbial biofilms" *Applied Microbiology and Biotechnology* 90:1869-1881 (2011).

Kaufmann et al. "Separation of the Rotational Isomers of Tetrakis(N-methyl-2-pyridiniumyl)porphyrin and Crystal Structure of α,α,α,β-(Tetrakis(N-methyl-2-pyridiniumyl)porphyrin)copper Hexacyanoferrate" *Inorganic Chemistry* 34:5073-5079 (1995).

Makinde et al. "Effect of a Metalloporphyrin Antioxidant (MnTE-2-PyP) on the Response of a Mouse Prostate Cancer Model to Radiation" *Anticancer Research* 29:107-118 (2009).

Munroe et al. "Only one of a wide assortment of manganese-containing SOD mimicking compounds rescues the slow aerobic growth phenotypes of both *Escherichia coli* and *Saccharomyces cerevisiae* strains lacking superoxide dismutase enzymes" *Journal of Inorganic Biochemistry* 101(11-12):1875-1882 (2007).

Musk et al. "Chemical Countermeasures for the Control of Bacterial Biofilms: Effective Compounds and Promising Targets" *Current Medicinal Chemistry* 13:2163-2177 (2006).

Oberley-Deegan et al. "The Antioxidant Mimetic MnTE-2-PyP, Reduces Intracellular Growth of *Mycobacterium abscessus*" *American Journal of Respiratory Cell and Molecular Biology* 41:170-178 (2009).

Rajic et al. "A new SOD mimic, Mn(III) *ortho N-butoxyethylpyridylporphyrin*, combines superb potency and lipophilicity with low toxicity" *Free Radical Biology & Medicine* 52:1828-1834 (2012).

Reboucas et al. "Pure manganese(III) 5,10,15,20-tetrakis(4-benzoic acid)porphyrin (MnTBAP) is not a superoxide dismutase mimic in aqueous systems: a case of structure-activity relationship as a watchdog mechanism in experimental therapeutics and biology" *Journal of Biological Inorganic Chemistry* 13:289-302 (2008).

Reboucas et al. "Quality of potent Mn porphyrin-based SOD mimics and peroxynitrite scavengers for pre-clinical mechanistic/therapeutic purposes" *Journal of Pharmaceutical and Biomedical Analysis* 48:1046-1049 (2008).

Richards et al. "Observation of a Stable Water-Soluble Lithium Porphyrin" *Inorganic Chemistry* 35:1940-1944 (1996).

Rogers et al. "Tandem dispersion and killing of bacteria from a biofilm" *Organic & Biomolecular Chemistry* 7:603-606 (2009).

Spasojevic et al. "Pharmacokinetics of the potent redox modulating manganese porphyrin, MnTE-2-PyP$^{5+}$ in plasma and major organs of B6C3F1 mice" *Free Radical Biology and Medicine* 45(7):943-949 (2008).

Tyle, Praveen "Iontophoretic Devices for Drug Delivery" *Pharmaceutical Research* 3(6):318-326 (1986).

Van Der Wielen et al. "Changes in the penile arteries of the rat after fractionated irradiation of the prostate: a pilot study" *The Journal of Sexual Medicine* 6(7):1908-1913 (2009) (Abstract Only).

Wood et al. "Engineering biofilm formation and dispersal" *Trends in Biotechnology* 29(2):87-93 (2011).

Hisasue. "Erectile dysfunction following external beam radiotherapy for clinically organ-confined or locally advanced prostate cancer." Jpn J Clin Oncol. May 2004:34(5):269-73.

METHODS OF TREATING ERECTILE DYSFUNCTION

RELATED APPLICATIONS

This application is a divisional of U.S. patent application Ser. No. 14/892,740, filed Nov. 20, 2015, now allowed, which is a 35 U.S.C. § 371 national phase entry of International Application No. PCT/US2014/053442, filed Aug. 29, 2014, and which claims the benefit of U.S. Provisional Patent Application Ser. No. 61/872,991, filed Sep. 3, 2013, the disclosure of each of which is incorporated herein by reference in its entirety.

BACKGROUND OF THE INVENTION

Prostate cancer is among the most common forms of cancer in men, and is frequently treated with radiation therapy (alone, or in combination with other forms of treatment such as chemotherapy and surgery). Unfortunately, common side effects of prostate cancer treatment include incontinence and erectile dysfunction. Given the wide-spread prevalence of prostate cancer, there is accordingly a need for new approaches to treating these side effects.

SUMMARY OF THE INVENTION

A method of treating erectile dysfunction and/or incontinence following pelvic radiation treatment in a subject in need thereof (e.g., a subject administered radiation treatment for cancer) is provided herein. The method comprises administering the subject an active agent as described herein in an amount effective to treat erectile dysfunction and/or incontinence in the subject following the pelvic radiation treatment.

A still further aspect of the present invention is an active agent as described herein for use in a method of treatment as described herein, or for use in the preparation of a medicament for carrying out a method of treatment as described herein.

The present invention is explained in greater detail in the specification set forth below. The disclosures of all United States Patents cited herein are incorporated herein by reference.

DETAILED DESCRIPTION OF PREFERRED EMBODIMENTS

Figure 1:
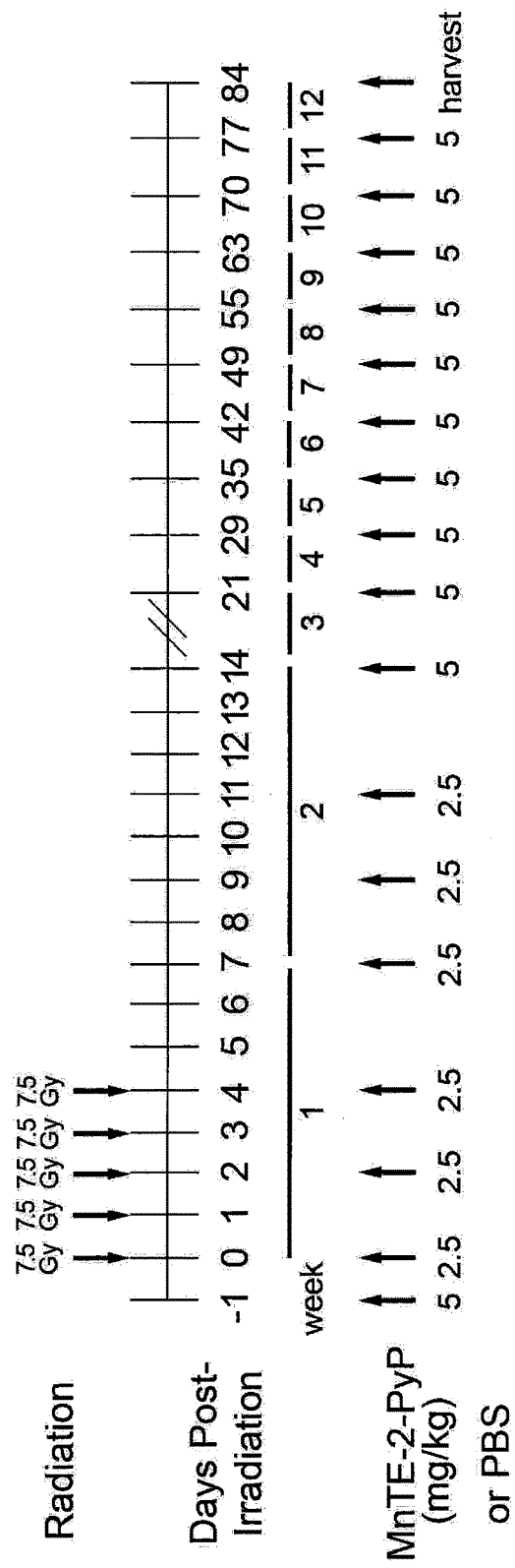
FIG. 1. Diagram of Experimental Design. Rats received 5 consecutive radiation doses of 7.5 Gy to the lower abdomen. Rats were injected i.p. with MnTE-2-PyP or PBS as a control throughout the study as indicated. Animals were harvested 12 weeks post-irradiation. There were four animals per group and the experiment was repeated once.

The present invention is primarily concerned with the treatment of human subjects, but the invention may also be carried out on animal subjects, particularly mammalian subjects such as dogs, cats, livestock and horses for veterinary purposes. While subjects may be of any suitable age, the subjects are in some embodiments neonatal, infant, juvenile, adolescent, adult, or geriatric subjects.

"Treat" as used herein refers to any type of treatment that imparts a benefit to a patient or subject matter as described herein, particularly delaying or retarding the onset or progression of the conditions described herein, or reducing the severity of symptoms, or speeding or improving recovery therefrom.

"Pharmaceutically acceptable" as used herein means that the compound or composition is suitable for administration to a subject to achieve the treatments described herein, without unduly deleterious side effects in light of the severity of the disease and necessity of the treatment.

"Combination" as used herein with respect to a method of administration (e.g., an active compound and an antibiotic administered in combination) includes administering the the two or more compounds simultaneously, or sequentially, sufficiently close in time to produce a combined therapeutic or treatment effect.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino; heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

1. Active Compounds/Active Agents.

Active compounds or active agents of the present invention are, in general, porphyrin compounds. The active compounds include superoxide dismutase (SOD) mimetic prophryin compounds, and/or redox active porphyrin compounds.

Examples of porphyrin active compounds, and methods of making the same, include but are not limited to those set forth in U.S. Pat. No. 8,470,808 to Piganelli et al.; U.S. Pat. No. 8,183,364 to Batinic-Haberle et al., U.S. Pat. No. 6,916,799 to Fridovich et al.; U.S. Pat. No. 6,479,477 to Crapo et al.; U.S. Pat. No. 6,583,132 to Crapo et al. and in US Patent Application Pub. No. US 2012/0065181 to Warner et al.; the disclosures of which are incorporated by reference herein in their entirety.

Examples of active compounds include but are not limited to compounds of Formula I:

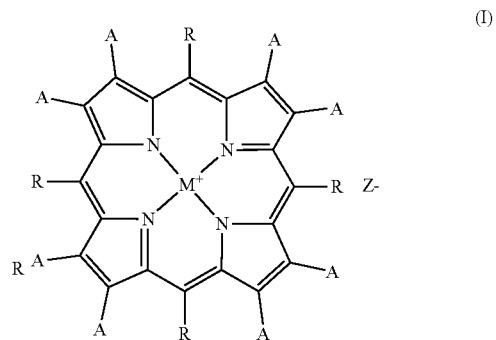

(I)

wherein:

each R is independently substituted or unsubstituted aryl, heteroaryl, cycloalkyl, or heterocycloalkyl;

each A is an independently selected hydrogen, or an electron-withdrawing or electron donating group (e.g., e.g., is halogen, NO$_2$ or CHO), M is a metal, e.g., selected from the group consisting of manganese, iron, copper, cobalt, nickel and zinc, or is absent (in which case a hydrogen is added to each of the two nitrogens required to correct valency), and Z$^-$ is a counterion.

In some embodiments of Formula I above, each R is preferably heteroaryl or heterocycloalkyl, particularly those containing at least one or two nitrogen atoms in the heterocyclic ring (e.g., pyrrolyl, imidazolyl, triazolyl, pyridyl, pyrimidyl, triazinyl, oxazolyl, thiazolyl, oxazinyl, thiazinyl, oxathiazinyl, etc.), in some embodiments wherein at least one of which nitrogen atoms (or in some embodiments at least two of which nitrogen atoms) are optionally but preferably substituted (e.g., quaternized) with a substituent such as described in connection with heterocyclic groups above (e.g., substituted with alkyl, alkoxyalkyl, etc.).

Still more particular examples of the foregoing active compounds include but are not limited to those set forth below.

A. Alkyl Substituted Imidazole Porphyrins.

In some embodiments the active compound has a structure of Formula A1 or A2:

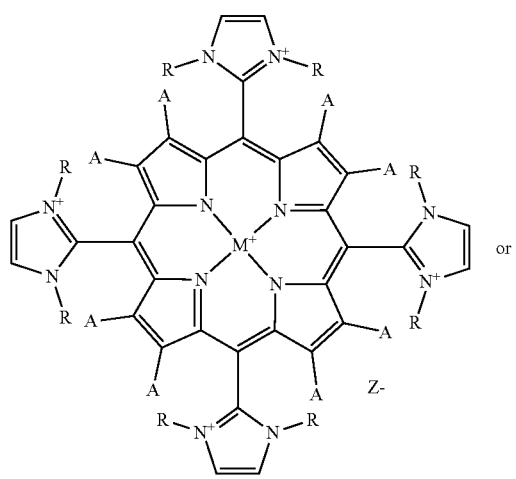

(A1)

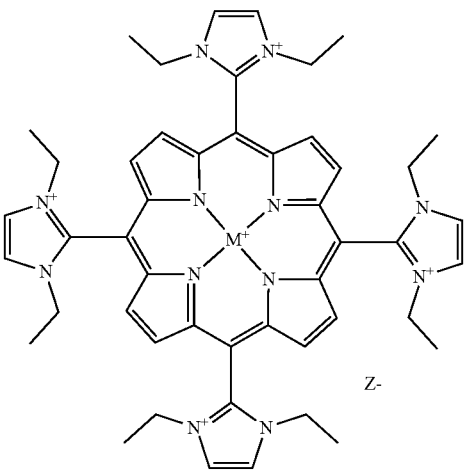

wherein $Z^-$ is a counterion.

B. Alkyl Substituted Pyridyl Porphyrins

In some embodiments the active compound has a structure of Formula B1 or B2:

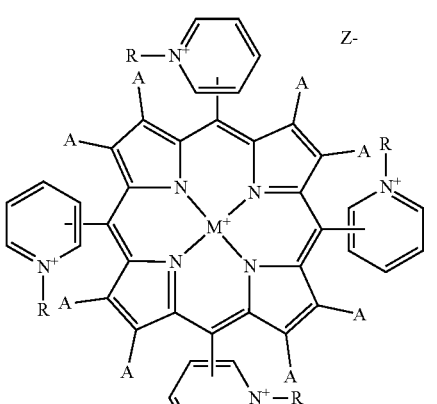

(B1)

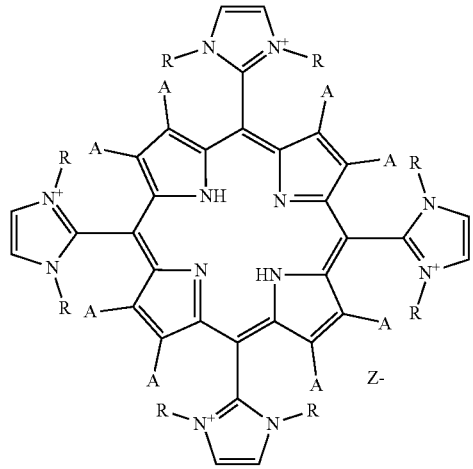

(A2)

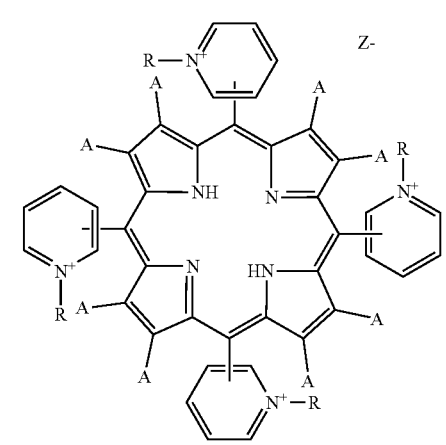

(B2)

wherein:

each R is $C_{1-12}$ alkyl (straight chain or branched), more preferably $C_{2-6}$ alkyl, and most preferably ethyl, propyl, butyl, or pentyl (straight chain or branched);

each A is, independently, hydrogen or an electron withdrawing group (e.g., halogen, $NO_2$ or CHO), M is metal selected from the group consisting of manganese, iron, copper, cobalt, nickel and zinc, and $Z^-$ is a counterion.

In some embodiments the active compound has the formula:

wherein:

each R is $C_{1-12}$ alkyl (straight chain or branched), more preferably $C_{2-6}$ alkyl, and most preferably ethyl, propyl, butyl, or pentyl (straight chain or branched);

each A is, independently, hydrogen or an electron withdrawing group (e.g., halogen, $NO_2$ or CHO), M is metal selected from the group consisting of manganese, iron, copper, cobalt, nickel and zinc, and Z⁻ is a counterion.

In some embodiments the compound has a structure of the Formula V:

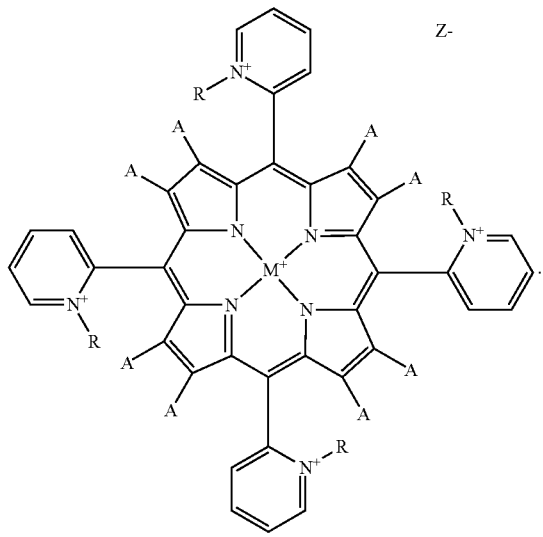

V wherein each R, A, M and Z is as given in connection with Formula B1 and B2 above.

In some embodiments the compound has the structure:

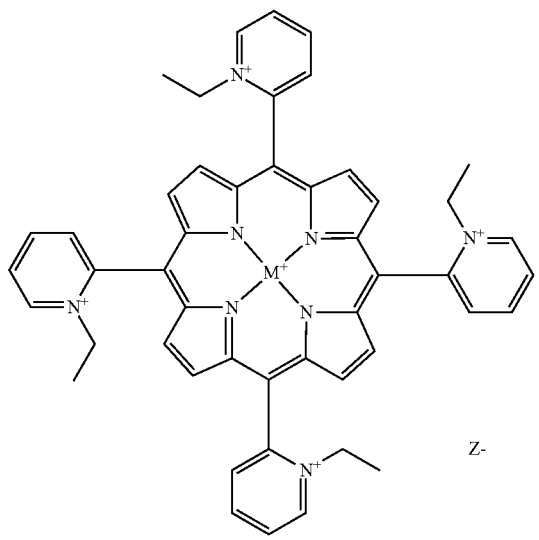

wherein Z⁻ is a counterion.

C. Alkoxyalkyl Substituted Pyridyl Porphyrins.

In some embodiments the active compound has a structure of Formula C1 or C2:

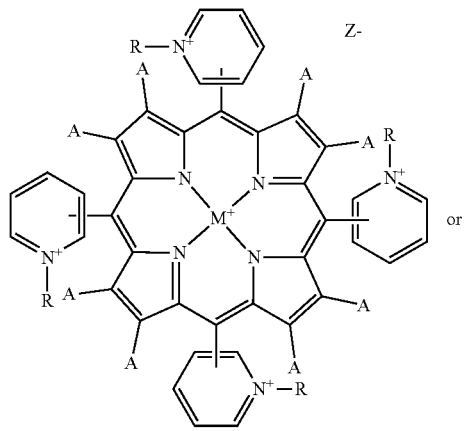

(C1)

or

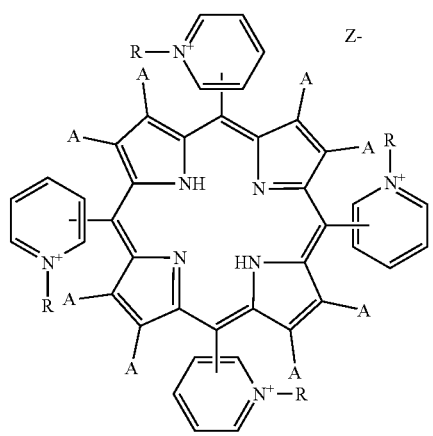

(C2)

wherein:

each R is —(CH$_2$)$_m$CH$_2$OX;

m is 1 or 2, preferably 1;

X is C$_{1-12}$ alkyl (straight chain or branched), more preferably C$_{2-6}$ alkyl, and most preferably ethyl, propyl, butyl, or pentyl (straight chain or branched).

each A is, independently, hydrogen or an electron withdrawing group (e.g., halogen, NO$_2$ or CHO), M is metal selected from the group consisting of manganese, iron, copper, cobalt, nickel and zinc, and Z⁻ is a counterion.

In some embodiments the compound has a structure of the Formula V:

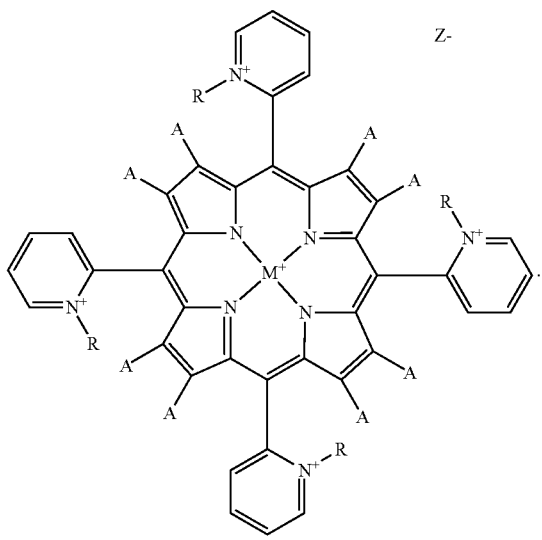

wherein each R, A, M and Z is as given in connection with Formula C1 and C2 above.

In some embodiments the compound has the structure:

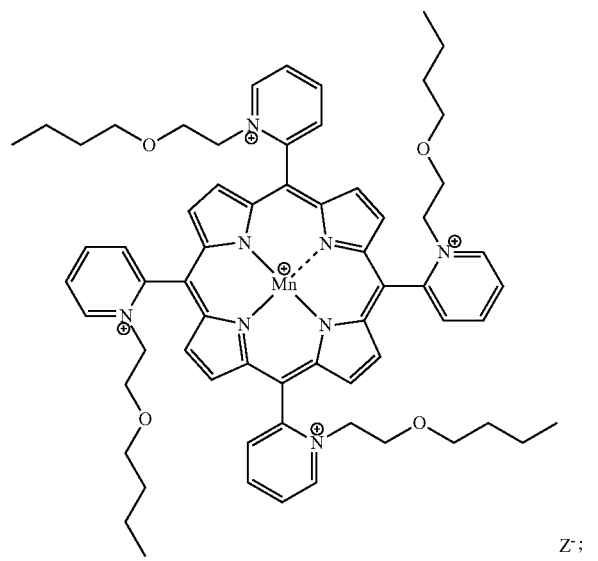

wherein $Z^-$ is a counterion.

D. Salts.

The active compounds disclosed herein can, as noted above, be prepared in the form of their salts or pharmaceutically acceptable salts, e.g., to provide a compound or composition including a counterion as noted above. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth;

and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The effective amount (e.g., therapeutically effective or treatment effective amount) or dosage of any specific active compound as described herein, for use in any specific method as described herein, will vary depending on factors such as the condition being treated, the route of administration, the general condition of the subject (e.g., age, gender, weight, etc.), etc. In general (e.g., for oral or parenteral administration), the dosage may be from about 0.01, 0.05, or 0.1 milligram per kilogram subject body weight (mg/kg), up to about 1, 5, or 10 mg/kg. For topical administration, the active agent may be included in a pharmaceutically acceptable composition to be applied in any suitable amount, typically from 0.01, 0.1, or 1 percent by weight, up to 10, 20, or 40 percent by weight, or more, of the weight of the composition, again depending on factors such as the condition being treated, condition of the subject, etc.

The active agents described herein may be administered directly or through the administration to the subject of a pharmaceutically acceptable prodrug which is in turn converted to the active agent in vivo. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

4. Treating Radiation-Induced Erectile Dysfunction and/or Incontinence.

As noted above, the present invention provides a method of treating erectile dysfunction and/or incontinence (including both urinary and bowel incontinence) following pelvic radiation or irradation treatment. The subject may be a male subject who has received pelvic radiation or irradiation treatment for prostate cancer; a female subject who has received pelvic radiation or irradiation treatment for cervical cancer, uterine cancer, or endometrial cancer; or a male or female subject who has received pelvic radiation or irradation treatment for other cancers located in the pelvic region (e.g., for colorectal cancer or bladder cancer).

The radiation treatment may comprise or have comprised external beam radiation, radioactive seed implantation therapy (brachytherapy), or a combination thereof.

The cancer may comprise or have comprised adenocarcinoma or small cell carcinoma, and may comprise or have comprised Stage I, Stage IIA, Stage IIB, Stage III, or Stage IV cancer.

The active agent may be administered on any suitable schedule, including prior to the onset of radiation treatment, during radiation treatment, and/or following radiation treatment of the subject. The active agent may be administered in the dosages described above on any suitable schedule, e.g., once, twice, or three times daily, for any suitable duration, typically from 1 or 2 weeks, up to 1 or 2 months or more, depending on the duration of the radiation treatment, and when administration of the active agent is initiated.

The present invention is explained in greater detail in the following non-limiting Examples.

Experimental 1

Manganese (III) Meso-Tetrakis-(N-Methylpyridinium-2-yl) porphyrin (MnTE-2-PyP) prevents side-effects Incurred by Pelvic Irradiation To test whether MnTE-2-PyP would protect the urogenital system from damage associated with pelvic irradiation, rats were exposed to fractionated irradiation of the pelvic region with and without MnTE-2-PyP administration. Animals were harvested 12 weeks post-irradiation and it was found that MnTE-2-PyP protected the structure and function of organs exposed to radiation. Specifically, MnTE-2-PyP protected the skin, prostate, testes, and penile tissues from irradiation-induced damage and prevented the loss of erectile function caused by radiation therapy.

Materials and Methods
Experimental Animals.
Sprague-Dawley rats (100-150 g, 4-6 weeks in age) from either Jackson or Harlan Laboratories were used in this study. Rats were housed at either the University of Colorado Anschutz Medical Campus or at National Jewish Health and given a continuous supply of food and water. This study was carried out in strict accordance with the recommendations of the Guide for the Care and Use of Laboratory Animals of the National Institutes of Health. All treatments and procedures were approved by the institutional animal care and use committees at the two institutions.

Treatment Groups and Experimental Design.

Animals were randomly assigned to 4 groups (8 rats per group): 1) PBS injected with no irradiation, 2) MnTE-2-PyP injected with no irradiation, 3) PBS injected with irradiation, and 4) MnTE-2-PyP injected with irradiation. The experimental design is illustrated in FIG. 1. Briefly, animals were injected with MnTE-2-PyP (5 mg/kg) or PBS 24 hours before the start of radiation. Rats were irradiated for 5 sequential days with 7.5 Gy/day in the lower pelvic region. Animals were positioned under a lead shield such that only the lower pelvic region received radiation. Radiation was delivered by X-ray irradiation at a dose rate of 1 Gy per minute. This irradiation scheme was chosen because it mimics an irradiation scheme that a patient undergoing prostate cancer therapy would undertake to eradicate the prostate tumor (G. van der Wielen et al., J Sex Med 6: 1908-1913). MnTE-2-PyP (2.5 mg/kg) or PBS was administered every other day for the following two weeks. The animals were then administered MnTE-2-PyP (5 mg/kg) or PBS once a week until 12 weeks post-irradiation. The rats weights and radiation-induced skin damage was documented once a week. At the 12 week time point, the erectile function of the rats was accessed and tissues (prostate and penis) were harvested from the animals. This experiment was repeated once with the same groups and time points.

MnTE-2-PyP Treatment.

MnTE-2-PyP was synthesized by Ricerca Biosciences, LLC. Concord, Ohio, USA. MnTE-2-PyP was dissolved in PBS and injected (100 µl) intraperitoneally (i.p.) at 2.5 or 5 mg/kg at the above specified times. PBS (100 µl) injected i.p. was used as a control.

Pharmacokinetics of MnTE-2-PyP in Rat Urogenital System.

The same MnTE-2-PyP dosing scheme was used for pharmacokinetic analysis as was used for the experimental design with a different cohort of animals. There were four groups of animals and each group had 3 rats: group 1) rats were harvested 1 week after the start of injections, group 2) rats were harvested 2 weeks after the start of injections, group 3) rats were harvested 12 weeks after the start of injections (harvested 7 days after the last injection), group 4) rats were harvested 12 weeks+one day after the start of injections (harvested 1 day after the last injection). At each time point, the liver, bowel, prostate, penile tissue and bladder were collected and flash frozen. The MnTE-2-PyP concentrations were then determined by the PK/PD Bioanalytical Core Laboratory at the Duke Cancer Institute as previously described (I. Spasojevic et al., Free Radic Biol Med 45: 943-949).

Scoring of Skin Reaction to Irradiation.

Animals were observed through the course of the experiment. They received a score from a reaction scale from Hall and Giaccia [24]. 0=no visible reaction, 1=faint erythema, 2=erythema, 3=marked erythema, 4=moist desquamation of less than half of the irradiated area, 5=moist desquamation of more than half the irradiated area.

Histology of Rat Urogenital System.

Rat tissues (prostate and penis) were fixed in 4% paraformaldehyde and embedded in paraffin. The tissue blocks were sectioned (5 µm thick), deparafinized in xylene and rehydrated through sequential steps of 100, 95, and 75% ethanol. The sections were stained with hematoxylin and eosin, dehydrated and coverslips mounted. Penile tissue was also stained with trichrome (Sigma, St. Louis, Mo.) to visualize fibrosis, according to the manufacturer's protocol.

Immunohistochemistry.

Immunohistochemistry was performed utilizing standard DAB techniques (Vector Labs, Burlingame, Calif.). Paraffin blocks were sectioned, deparafinized, and rehydrated. Antigens were unmasked with preheated antigen retrieval in sodium citrate buffer for 20 min and then cooled. $H_2O_2$ (3%) was placed on the slides for 5 minutes to block endogenous peroxides, followed by a serum block for 30 minutes. The 8-OHdG primary antibody (Abcam, Cambridge, Mass., 5 μg/mL) was then added overnight at the indicated dilution. Biotinylated mouse secondary antibody (1:200) was then added for 45 minutes. Biotin binding was increased using the ABC Elite method for 30 min and stains were visualized with DAB. The tissues were counterstained with hematoxylin, dehydrated and coversliped. The 8-OHdG stained sections were quantified by taking 10 random pictures of each prostate section. The sections were scored blindly, and any nuclear staining was counted as a positive 8-OHdG stained cell.

Erectile Functional Assay.

The erectile functional assay was performed in rats 12 weeks post-irradiation, as previously described (J. Dall'Era et al., Int J Impot Res 20: 307-314.). Briefly, rats were anesthetized with sodium pentobarbital before dissection of the lower abdomen to locate the cavernous nerve. Two stainless steel electrodes were placed around the cavernous nerve on one side, with the negative electrode approximately 1 mm from the positive electrode. The skin overlaying the penis was removed and the crura were dissected free. A 26-gauge needle that was connected to a pressure transducer and was inserted into either the right or left crus. Electrostimulation was performed using a stimulator (World Precision Instruments, Sarasota, Fla., USA). Increases in intracavernous pressure were measured and recorded using the Data-Trax data acquisition software (Distributed Design Concepts, Dover, N.H., USA).

Results

Figure 2:
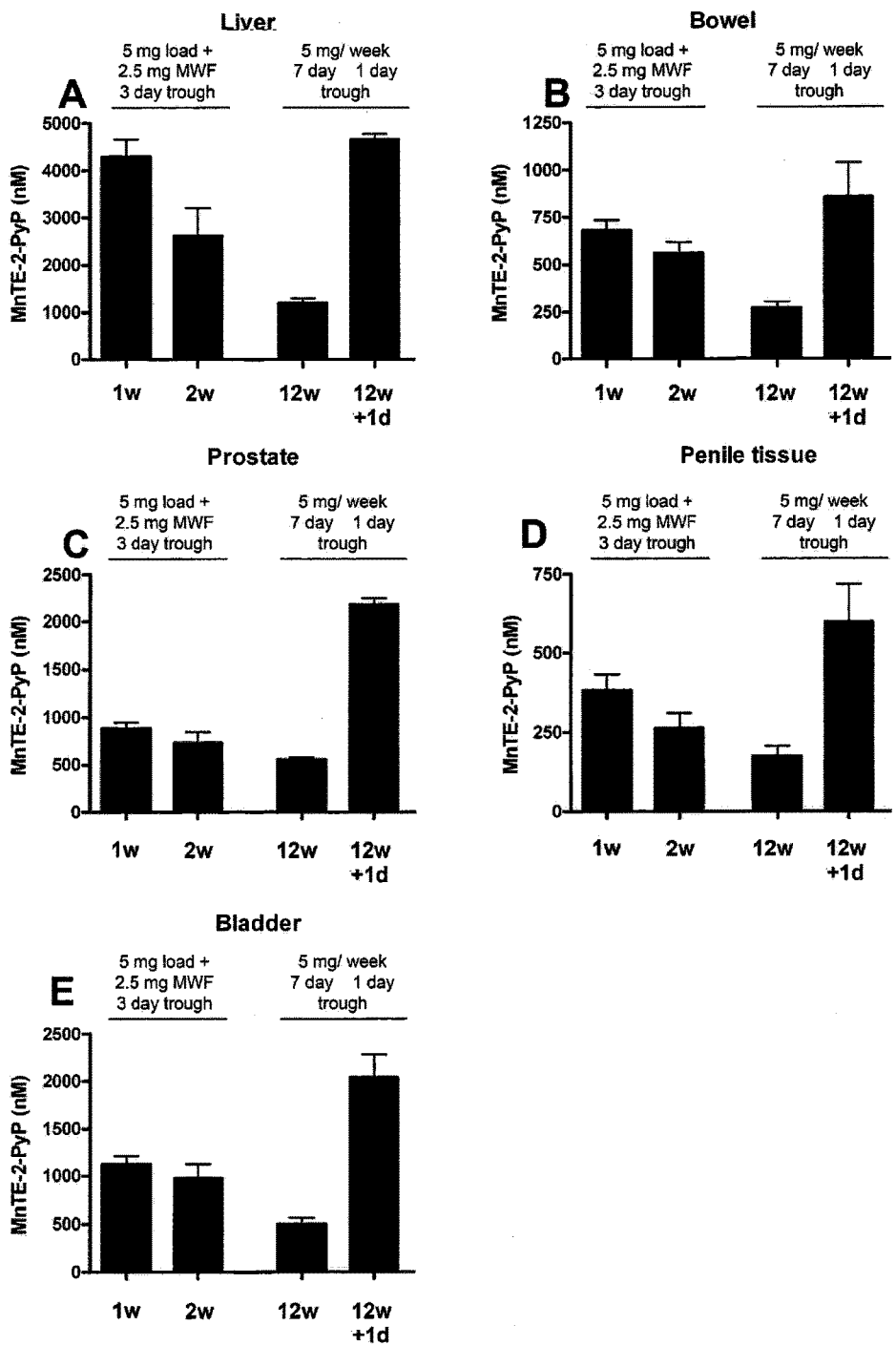
FIG. 2. Pharmacokinetics of MnTE-2-PyP in the rat urogenital system. Rats received injections of MnTE-2-PyP as outlined in FIG. 1 and harvested 1 week, 2 weeks, 12 weeks and 12 weeks+1 day after the start of injections. Rats harvested at 1 and 2 weeks had not received an injection for 3 days (3 day trough). Rats harvested at 12 weeks, had not received an injection for 7 days (representing the lowest levels during the week) and 12 weeks+1 day represent rats 1 day after an injection (representing the highest levels during the week). A. Liver. B. Bowel. C. Prostate. D. Penile tissues. E. Bladder. MnTE-2-PyP was detected in the liver, bowel, prostate, penile tissue and bladder. Data represents the mean±standard error of the mean, n=3 per time point.

Pharmacokinetic analysis was performed to ensure that adequate levels of MnTE-2-PyP would reach the urogenital tissues when administered intraperitoneally (i.p.). Rats were subjected to the same MnTE-2-PyP dosing scheme (FIG. 1) as the animals undergoing irradiation and tissues were harvested 1 week, 2 weeks, 12 weeks, and 12 weeks+one day after the start of drug administration. The liver, bowel, prostate, penis, and bladder tissues all contained MnTE-2-PyP at every time point investigated (FIG. 2). The liver contained the highest concentration of MnTE-2-PyP, which is not surprising since MnTE-2-PyP is known to accumulate in the liver (I. Spasojevic et al., Free Radic Biol Med 45: 943-949). The bowel, prostate, and bladder all had similar levels of MnTE-2-PyP (~1000 nM) over the course of the pharmacokinetic analysis. This concentration of MnTE-2-PyP has been shown to prevent free radical damage in other tissue types, including the lung (I. Spasojevic et al., Free Radic Biol Med 45: 943-949; B. Gauter-Fleckenstein et al., Free Radic Biol Med 48: 1034-1043). Penile tissues had the lowest levels of MnTE-2-PyP, but were still detectable. We conclude that adequate levels of MnTE-2-PyP are able to reach the urogenital system when MnTE-2-PyP is administered i.p.

Figure 3:
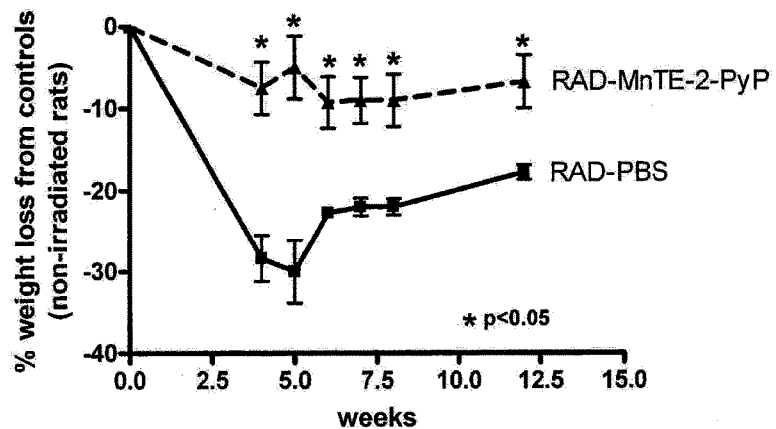
FIG. 3. Irradiated rats receiving MnTE-2-PyP lost significantly less weight than irradiated rats injected with PBS. Weights of irradiated animals throughout the course of the experiment as compared to their respective non-irradiated groups. n=8 rats per group, asterisk (*) denotes p<0.05.

A known side-effect of radiation exposure is weight loss. Animals were weighed throughout the course of the experiment (FIG. 3). Irradiated rats lost on average 23.9% more weight than non-irradiated rats. Irradiated rats injected with MnTE-2-PyP only lost 5.9% more weight than MnTE-2-PyP injected, non-irradiated, control animals. The irradiated rats receiving MnTE-2-PyP lost significantly less weight as compared to irradiated rats not receiving MnTE-2-PyP at all time points measured (FIG. 3).

Throughout the course of the experiment, phenotypic changes were observed between the treatment groups. Epilation was observed in the lower abdominal region in irradiated rats (data not shown); however, treatment with MnTE-2-PyP markedly blocked epilation in the radiation exposed area (data not shown). The skin of PBS injected irradiated rats had significantly more erythma and moist desquamation as compared to the skin of irradiated animals injected with MnTE-2-PyP (data not shown). An additional observation was a significant radiation-induced atrophy of the rat testes at 12 weeks post-irradiation (data not shown). The testes were ~40% the size of non-irradiated testes. However, we did not observe a change in the testis size in irradiated rats receiving MnTE-2-PyP compared to control, suggesting that MnTE-2-PyP also protects the testis from radiation-induced atrophy/damage.

At 12 weeks post-radiation therapy, histological analysis was performed on the prostate and penile tissues. Representative images of hematoxylin and eosin staining within the prostate demonstrate that MnTE-2-PyP protected the prostate epithelial glands from atrophy and loss of prostatic epithelial architecture in the irradiated rats (data not shown). Moreover, penile tissues were stained using Masson's trichrome stain to characterize tissue fibrosis. The trichrome staining revealed that MnTE-2-PyP prevented radiation-induced loss of smooth muscle and accumulation of collagen in penile tissues (data not shown), suggesting that MnTE-2-PyP protects penile tissue from radiation-induced fibrosis.

Figure 4:
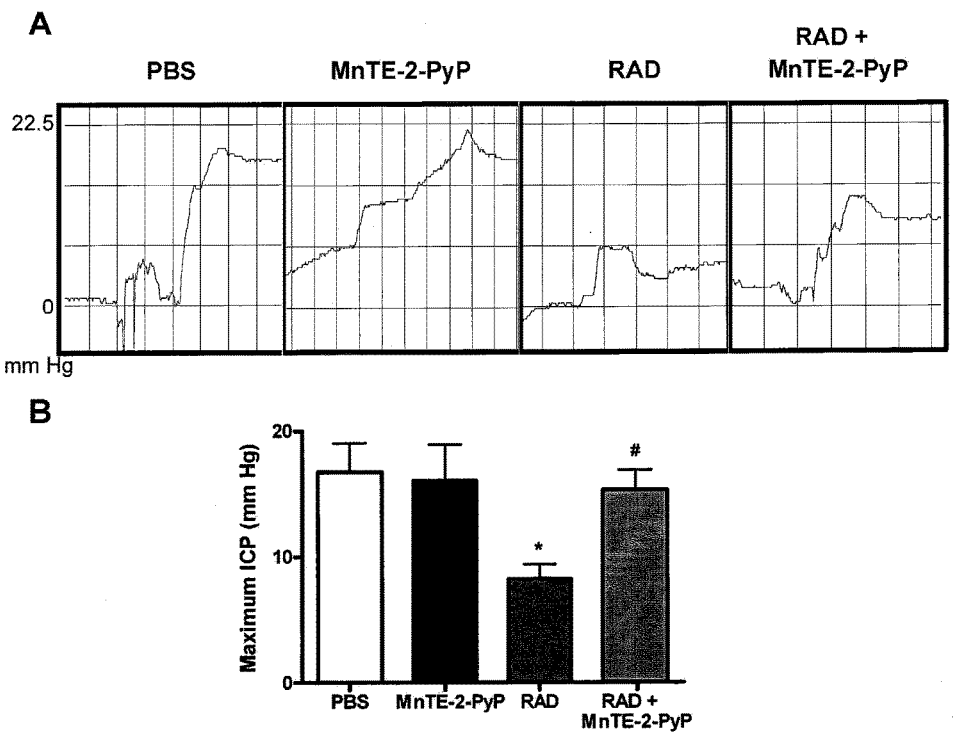
FIG. 4. Measuring erectile function in rats. Intracavernous pressure (ICP) was obtained after cavernous nerve stimulation as a measurement of erectile function 12 weeks post-irradiation. A. Representative pressure curves obtained after nerve stimulation. B. Maximum ICP obtained after cavernous nerve stimulation. Irradiation caused a significant decrease in ICP (RAD group) as compared to the non-irradiated group (PBS). MnTE-2-PyP significantly protected from the irradiation-induced loss in ICP (MnTE-2-PyP RAD). n=8 rats/group, asterisk (*) denotes significant difference from PBS group, p<0.05 and the number symbol (#) denotes significant difference from RAD group, p<0.05.

Erectile dysfunction is a common side-effect associated with prostate cancer radiation therapy. In our radiation model, we observed significant reduction in the intracavernous pressure in rat penises 12 weeks post-irradiation as compared to non-irradiated saline controls (FIG. 4). A reduction in intracavernous pressure is a direct measure of erectile dysfunction. Irradiated rats lost >50% of their intracavernous pressure; however, the irradiated rats receiving MnTE-2-PyP were completely protected from intracavernous pressure loss. Thus, MnTE-2-PyP served to protect against radiation-induced erectile dysfunction.

The foregoing is illustrative of the present invention, and is not to be construed as limiting thereof. The invention is defined by the following claims, with equivalents of the claims to be included therein.

That which is claimed is:

1. A method of treating or inhibiting the development of erectile dysfunction and/or incontinence following pelvic radiation treatment in a subject in need thereof, comprising administering to said subject an active agent in a treatment effective amount, wherein said active agent is a compound of Formula C1:

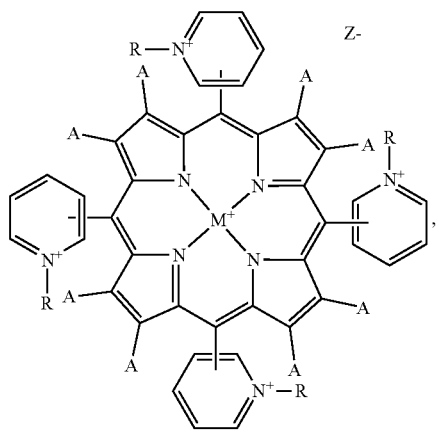

wherein:
- each R is —(CH$_2$)$_m$CH$_2$OX;
- m is 1 or 2;
- X is C$_{1-12}$ alkyl;
- each A is, independently, hydrogen or an electron withdrawing group;
- M is metal selected from the group consisting of manganese, iron, copper, cobalt, nickel and zinc, and
- Z$^-$ is a counterion or a pharmaceutically acceptable salt thereof.

2. The method of claim 1, wherein said treatment includes radiation treatment and said active agent is administered to said subject:
- prior to the onset of radiation treatment of said subject,
- during radiation treatment of said subject, and/or
- following radiation treatment of said subject.

3. The method of claim 1, wherein said radiation treatment comprises external beam radiation, radioactive seed implantation therapy (brachytherapy), or a combination thereof.

4. The method of claim 1, wherein said radiation treatment is for prostate cancer, cervical cancer, colorectal cancer, bladder cancer, uterine cancer, or endometrial cancer in said subject.

5. The method of claim 4, wherein said prostate cancer comprises Stage I, Stage IIA, Stage IIB, Stage III, or Stage IV prostate cancer.

6. The method of claim 1, wherein said compound has the structure:

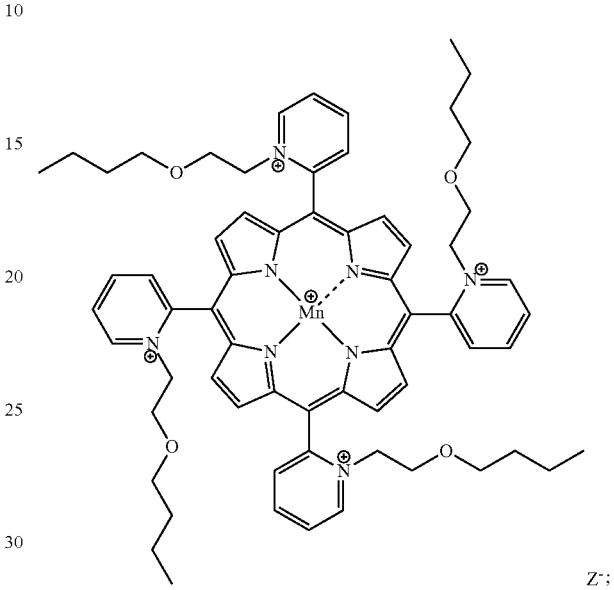

wherein Z$^-$ is a counterion.

7. The method of claim 1, wherein said active agent is administered to said subject in an amount from about 0.01 milligram per kilogram subject body weight (mg/kg) to about 10 mg/kg.

* * * * *